(12) United States Patent
Williams et al.

(10) Patent No.: US 7,208,511 B2
(45) Date of Patent: Apr. 24, 2007

(54) MICROBICIDAL COMPOSITION

(75) Inventors: Terry Michael Williams, Lower Gwynedd, PA (US); Li-Liang Shen Chia, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/859,647

(22) Filed: Jun. 3, 2004

(65) Prior Publication Data

US 2005/0020649 A1  Jan. 27, 2005

Related U.S. Application Data

(60) Provisional application No. 60/489,698, filed on Jul. 24, 2003.

(51) Int. Cl.
*A01N 43/80* (2006.01)
*A01N 37/18* (2006.01)

(52) U.S. Cl. ..................................... 514/372; 514/619
(58) Field of Classification Search ................ 514/372, 514/619
See application file for complete search history.

(56) References Cited

U.S. PATENT DOCUMENTS 3,929,562 A  12/1975  Shema et al.

FOREIGN PATENT DOCUMENTS

| EP | 0503175 | | 9/1992 |
|---|---|---|---|
| EP | 0503175 | A1 * | 9/1992 |
| JP | 2000-319113 | A * | 11/2000 |
| JP | 200319113 | A | 11/2000 |

* cited by examiner

*Primary Examiner*—San-Ming Hui
(74) *Attorney, Agent, or Firm*—Kenneth Crimaldi

(57) ABSTRACT

A microbicidal composition containing: (a) 2-methyl-4-isothiazolin-3-one; and (b) 2,2-dibromo-3-nitrilopropionamide.

6 Claims, No Drawings

MICROBICIDAL COMPOSITION

CROSS REFERENCE TO RELATED PATENT APPLICATIONS

This is a non-provisional application of now abandoned, U.S. provisional application Ser. No. 60/489,698 filed on Jul. 24, 2003.

This invention relates to a combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides. Combinations of different microbicides are sometimes used to provide overall control of microorganisms in a particular end use environment. For example, a combination of: (i) a 3:1 mixture of 5-chloro-2-methylisothiazolin-3-one and 2-methylisothiazolin-3-one; and (ii) 2,2-dibromo-3-nitrilopropionamide is disclosed in U.S. Pat. No. 3,929,562. However, there is a need for additional combinations of microbicides having enhanced activity against various strains of microorganisms to provide effective control of the microorganisms that is both quick and long lasting. Moreover, there is a need for combinations containing low levels of halogenated isothiazolones. The problem addressed by this invention is to provide such additional combinations of microbicides.

STATEMENT OF THE INVENTION

The present invention is directed to a microbicidal composition comprising: (a) 2-methyl-4-isothiazolin-3-one; and (b) 2,2-dibromo-3-nitrilopropionamide; wherein said composition contains no more than 12% halogenated 4-isothiazolone-3-ones.

DETAILED DESCRIPTION OF THE INVENTION

"MI" is 2-methyl-4-isothiazolin-3-one, also referred to by the name 2-methyl-3-isothiazolone. "DBNPA" is 2,2-dibromo-3-nitrilopropionamide.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, and MIC=minimum inhibitory concentration. Unless otherwise specified, temperatures are in degrees centigrade (° C.), and references to percentages (%) are by weight. "Salt-free" means that the composition contains zero or up to 0.5%, preferably zero or up to 0.1%, and more preferably zero or up to 0.01%, of metal salt, based on weight of the composition.

The compositions of the present invention unexpectedly have been found to provide enhanced microbicidal efficacy at a combined active ingredient level lower than that of the individual microbicides. The microbicidal compositions of the present invention contain relatively low levels of halogenated 3-isothiazolones, preferably no more than 5%, more preferably no more than 2%, more preferably no more than 1.2%, more preferably no more than 0.5%, and most preferably no more than 0.1%. Percentages of halogenated 3-isothiazolones in the composition of this invention are based on the total weight of active ingredients in the composition, i.e., the microbicides exclusive of any amounts of solvents, carriers, dispersants, stabilizers or other materials which may be present. Microbicidal compositions dependent on the presence of halogenated 3-isothiazolone are susceptible to chemical degradation and may require additional stabilizer components, such as the aforementioned metal salt stabilizers; salt stabilizers sometimes create unacceptable properties in finished formulations. For this reason it is desirable to provide microbicide formulations substantially free of halogenated 3-isothiazolone, but that still provide the degree of antimicrobial protection provided by the halogenated 3-isothiazolones; such are the microbicidal compositions of the present invention that are based on 2-methyl-3-isothiazolone, which do not require metal stabilizers.

Preferably, a weight ratio of 2-methyl-4-isothiazolin-3-one to 2,2-dibromo-3-nitrilopropionamide is from 150:1 to 1:10, more preferably from 100:1 to 1:7, more preferably from 10:1 to 1:1 and most preferably from 6:1 to 1:1.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

When a microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A microbicide component also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

The microbicides may be formulated separately or together. When both microbicides are each first formulated with a solvent, the solvent used for the first microbicide may be the same as or different from the solvent used to formulate the other commercial microbicide. It is preferred that the two solvents are miscible. In the alternative, the first microbicide and the other microbicide may be combined directly and then a solvent added to the mixture.

Those skilled in the art will recognize that the microbicide components of the present invention may be added to a locus sequentially, simultaneously, or may be combined before being added to the locus. It is preferred that the first microbicide and the second microbicide component be added to a locus simultaneously or combined prior to being added to the locus. When the microbicides are combined prior to being added to a locus, such combination may optionally contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms by introducing a microbicidally effective amount of the compositions onto, into, or at a locus subject to microbial attack. Suitable loci include, for example: cooling towers; air washers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the microbicidal compositions of the present invention are used to inhibit the growth of microorganisms at a locus selected from one or more of emulsions, dispersions, paints, latices, household products, cosmetics, toiletries, shampoos, soaps, detergents, machining fluids and industrial cleaners. In particular, the microbicidal compositions are useful in emulsions, dispersions, paints and latices.

When the synergistic compositions of the present invention are used in personal care compositions, the formulated compositions may also comprise one or more ingredients selected from UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents.

The specific amount of the composition of this invention necessary to inhibit or control the growth of microorganisms in a locus depends upon the particular locus to be protected. Typically, the amount of the composition of the present invention to control the growth of microorganisms in a locus is sufficient if it provides from 0.1 to 10,000 ppm active ingredient of the composition in the locus. It is preferred that the active ingredients of the composition be present in the locus in an amount of at least 0.5 ppm, more preferably at least 1 ppm, more preferably at least 10 ppm and most preferably at least 50 ppm. It is preferred that the active ingredients of the composition be present in the locus in an amount of no more than 5000 ppm, more preferably no more than 3000 ppm, more preferably no more than 1000 ppm, and most preferably no more than 500 ppm.

EXAMPLES

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538–541 (1961), using the ratio determined by the formula:

$$Q_a/Q_A + Q_b/Q_B = \text{Synergy Index ("SI")}$$

wherein:

$Q_A$=concentration of compound A (first component) in ppm, acting alone, which produced an end point (MIC of Compound A).

$Q_a$=concentration of compound A in ppm, in the mixture, which produced an end point.

$Q_B$=concentration of compound B (second component) in ppm, acting alone, which produced an end point (MIC of Compound B).

$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Synergy tests were conducted using standard microtiter plate assays with media designed for optimal growth of the test microorganism. Full-strength nutrient medium (Trypticase Soy Broth, TSB) or mineral salts-glucose medium (M9G) with added yeast extract was used for testing bacteria. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient. The combinations of the present invention were tested against three bacteria, *Pseudomonas aeruginosa* (*P. aeruginosa* —ATCC #15442), *Enterobacter aerogenes* (ATCC #13048), and *Kiebsiella pneumoniae* (ATCC #13883). The bacteria were used at a concentration of about $10^8$ bacteria per mL. These microorganisms are representative of natural contaminants in many consumer and industrial applications. The plates were visually evaluated for microbial growth (turbidity) to determine the MIC after various incubation times at 30° C.

To evaluate "Speed of Kill" an aliquot of 30 g of pH 8 TSB was dispensed in sterile 2 oz (60 mL) jars. Biocides stock solution was added into each jar to achieve the final concentration. The test samples were inoculated with 0.3 ml of mixed bacterial inoculum (resulting in $10^6$/ml bacteria per ml of test solution). Samples were then placed in a shaker water bath at 30° C. Bacterial growth was monitored via the microtiter MPN method using the BECKMAN AUTOMATIC 2000 Workstation after 30 min, 1, 4, 24, 48, 72 hours and again 6–7 days contact time. The microtiter plates were incubated at 30° C. for 2 days.

The test results for demonstration of synergy of the microbicide combinations of the present invention are shown below in the Tables. In each test, First Component (A) was MI and the Second Component (B) was DBNPA. "NG" means that no growth was observed. Each table shows the specific combinations of MI and the second component; results against the microorganisms tested with incubation times; the end-point activity in ppm measured by the MIC for MI alone ($Q_A$), for the second component alone ($Q_B$), for MI in the mixture ($Q_a$) and for second component in the mixture ($Q_b$); the calculated SI value; and the range of synergistic ratios for each combination tested (MI/second component or A/B).

TABLE I

MI Alone and in Combination with DBNPA vs Bacteria in TSB Medium

| PPM AI Added | | CFU/ml Bacteria Log Reduction vs Control after @ 30° C. for: | | | | | |
|---|---|---|---|---|---|---|---|
| MI | DBNPA | 30 min | 1 hr | 4 hr | 24 hr | 48 hr | 72 hr | 168 |
| 0 | 0 | | | | | | | |
| 25 | 0 | −0.3 | 0.0 | 0.2 | −1.3 | −2.0 | — | — |
| | 1 | −1.1 | 0.2 | 0.0 | −1.4 | — | — | |
| | 2 | 0.6 | −0.3 | −0.3 | −0.8 | — | — | |
| | 5 | −0.1 | 0.0 | 0.0 | −1.2 | −2.3 | — | |
| | 9 | 0.4 | 0.4 | 0.4 | 0.7 | −2.0 | — | |
| | 23 | 0.8 | −0.4 | 0.2 | 4.6 | >5.4 | 3.2 | −2.6 |
| 50 | 0 | 0.4 | 0.2 | 0.4 | −0.6 | −1.6 | — | — |
| | 1 | 0.4 | 0.0 | 0.4 | 0.0 | −2.0 | — | |
| | 2 | 0.2 | 0.0 | 0.0 | 0.4 | −1.0 | — | |
| | 5 | 0.4 | 0.6 | 0.0 | 0.7 | −2.0 | — | |
| | 9 | 0.4 | 0.2 | 0.0 | 1.1 | −1.0 | — | |
| | 23 | 0.6 | 0.4 | 0.4 | >5.4 | >5.4 | 5.0 | −2.6 |
| 75 | 0 | 0.2 | 0.2 | −0.3 | 0.2 | −2.0 | — | |
| | 1 | −0.1 | 0.0 | −0.3 | 1.2 | −1.6 | — | |
| | 2 | 0.6 | 0.2 | 0.4 | 0.8 | −2.3 | — | |
| | 5 | 0.2 | −0.3 | 0.0 | 1.2 | 0.0 | −2.3 | |
| | 9 | 0.6 | 0.7 | 0.2 | 1.0 | 0.0 | −0.8 | |
| | 23 | 0.6 | 1.0 | 0.4 | >5.4 | 4.0 | 4.9 | 0.4 |
| 100 | 0 | 0.4 | 0.6 | 0.2 | 0.8 | 1.7 | 0.0 | −2.8 |
| | 1 | 0.6 | 0.2 | 0.2 | 0.8 | 1.4 | 0.0 | −2.8 |
| | 2 | 0.2 | 0.4 | 0.2 | 1.0 | 1.6 | 0.2 | −2.8 |
| | 5 | −0.1 | 0.0 | 0.4 | 2.0 | 2.2 | 1.2 | −2.8 |
| | 9 | 0.6 | 0.2 | 0.7 | 2.0 | 1.7 | 1.0 | −2.6 |
| | 23 | −0.1 | 0.2 | 0.7 | >5.4 | >5.4 | >5.4 | 1.7 |
| 150 | 0 | 0.6 | 0.2 | 0.0 | −0.2 | 1.7 | 0.4 | −2.0 |
| | 1 | 0.2 | 0.0 | 0.7 | 1.4 | 2.0 | 1.0 | −2.0 |
| | 2 | 0.4 | −0.3 | 1.2 | 1.0 | 1.6 | 1.4 | −2.2 |
| | 5 | 0.6 | 0.0 | 0.7 | 1.6 | 2.0 | 2.2 | −2.2 |
| | 9 | 0.2 | 0.4 | 0.7 | 1.0 | 2.4 | 2.7 | −2.6 |
| | 23 | 0.6 | 0.2 | 1.2 | >5.4 | >5.4 | >5.4 | 1.2 |
| 0 | 1 | 0.6 | −0.6 | −1.0 | −2.6 | — | — | |
| | 2 | −0.1 | −0.3 | −0.8 | −1.4 | — | — | |
| | 5 | 0.4 | −0.3 | −1.6 | — | — | — | |
| | 9 | 0.4 | 0.0 | −1.0 | −2.0 | — | — | |
| | 23 | 0.4 | 0.2 | −1.0 | −1.4 | — | — | |

Log reduction was calculated based on bacterial reduction vs. 0 time untreated sample.
Detection limit × 1.1 log bacterial growth
Negative (−) log reduction values indicate growth.

TABLE II

Synergy of MI in Combination with DBNPA vs Mixed Bacteria in TSB in Speed of Kill Test (5-log reduction criteria used for synergy)

| | Minimum Effective Concentration (ppm AI) ALONE* | | Effective Concentration (ppm AI) IN COMBINATION | | |
|---|---|---|---|---|---|
| Time | MI | DBNPA | MI | DBNPA | S.I. |
| 24 hr | 300 | 46 | 50.0 | 23 | 0.67 |
| 48 hr | 300 | 46 | 25.0 | 23 | 0.58 |
| 72 hr | 300 | 46 | 50.0 | 23 | 0.67 |

*Minimum effective concentrations alone were determined by the method of Lazonby (when no end point value was measured, i.e., the highest level alone failed, the value reported in the table to represent a minimum effective level was 2× the highest level tested), see, e.g., U.S. Pat. No. 5,980,758.

TABLE III

Synergy Results of MI and DBNPA using the Minimum Inhibitory Concentration (MIC) Tests versus Mixed Bacteria

| | MIC Values (ppm AI) ALONE | | MIC Values (ppm AI) IN COMBINATION | | |
|---|---|---|---|---|---|
| Test Media | DBNPA | MI | DBNPA | MI | S.I. |
| 1/10 TSB | 45 | 38 | 8.1 | 19 | 0.68 |
| M9G + 0.1% yeast extract | 45 | 38 | 8.1 | 10 | 0.44 |
| M9G + 0.1% yeast extract | 45 | 38 | 16.2 | 2.5 | 0.43 |

MIC values determined after 24 hours at 30° C.

The invention claimed is:

1. A synergistic microbicidal composition comprising from 50 ppm to 1000 ppm of a biocide mixture comprising:
   (a) 2-methyl-4-isothiazolin-3-one; and
   (b) 2,2-dibromo-3-nitrilopropionamide;
   wherein said biocide mixture contains no more than 12% halogenated 4-isothiazolone-3-ones, and in which a weight ratio of 2-methyl-isothiazolin-3-one to 2,2-dibromo-3-nitrilopropionamide is from 150:1 to 75:23.

2. The composition of claim 1 in which the biocide mixture contains no more than 2% halogenated 4-isothiazolone-3-ones.

3. The composition of claim 2 in which the weight ratio of 2-methyl-4-isothiazolin-3-one to 2,2-dibromo-3-nitrilopropionamide is from 100:1 to 100:23.

4. The composition of claim 3 in which the biocide mixture contains no more than 1.2% halogenated 4-isothiazolone-3-ones.

5. The composition of claim 4 in which the biocide mixture contains no more than 0.5% halogenated 4-isothiazolone-3-ones.

6. The composition of claim 5 which is an emulsion, dispersion, paint, latex, aqueous metal working fluid or industrial process water.

* * * * *